United States Patent [19]
Fahl et al.

[11] Patent Number: 6,040,424
[45] Date of Patent: Mar. 21, 2000

[54] PROTEIN AND GENE FOR ANTIOXIDANT RESPONSE

[75] Inventors: William E. Fahl; Wyeth W. Wasserman, both of Madison, Wis.

[73] Assignee: Wisconsin Alumni Research Foundation, Madison, Wis.

[21] Appl. No.: 08/686,617

[22] Filed: Jul. 19, 1996

[51] Int. Cl.⁷ .................................................. C07K 14/435
[52] U.S. Cl. ............................................................ 530/350
[58] Field of Search .................................. 530/350; 514/2

[56] References Cited

PUBLICATIONS

Berenblum, et al., "The Modifying Influence of Dichloro–ethyl Sulphide on the Induction of Tumours in Mice by Tar," *Journ. of Path.* XXXII 425–434.

Favreau et al., "The Rat Quinone Reductase Antioxidant Response Element," *The Journal of Biological Chemistry* 270:24468–24474 (1995).

Friling, et al., "Xenobiotic–inducible expression of murine glutathione S–transferase Ya subunit gene is controlled by an electrophile–responsive element," *Proc. Natl. Acad. Sci. USA*, 87:6258–6262 (1990).

Friling, et al., "Two adjacent AP–1–like binding sites form the electrophile–responsive element of the murine glutathione S–transferase Ya subunit gene," *Proc. Natl. Acad. Sci. USA*, 89:668–672 (1992).

Hayes, et al., "The Glutathione S–Transferase Supergene Family: Regulation of GST and the Contribution of the Isoenzymes to Cancer Chemoprotection and Drug Resistance," *Critical Reviews in Biochemistry and Molecular Biology* 30:455–600 (1995).

Kensler, et al., "Oltipraz: Clinical Opportunities for Cancer Chemoprevention," *Journal of Cellular Biochemistry* Supplement 22:101–107 (1995).

Nguyen et al., "Transcriptional Regulation of a Rat Liver Glutanthions S–Transferase Ya Subunit Gene," *The Journal of Biological Chemistry* 269:13656–13662 (1994).

Prochaska, et al., "On the mechanisms of induction of cancer–protective enzymes: A unifying proposal," *Proc. Natl. Acad. Sci. USA* 82:8232–8236 (1985).

Rushmore, et al., "The Antioxidant Responsive Element," *The Journal of Biological Chemistry* 266:16632–16639 (1991).

Talalay, et al., "Identification of a common chemical signal regulating the induction of enzymes that protect against chemical carcinogenesis," *Proc. Natl. Acad. Sci. USA* 85:8261–8265 (1988).

Wattenberg, et al., "Chemoprevention of Cancer," *Cancer Research* 45:1–8 (1985).

Yoshioka et al. Antitumor promotion by phenolic antioxidants: Inhibition of AP–1 activity through induction of Fra expression. Proc. Natl. Acad. Sci. USA vol. 92, pp. 4972–4976, 1995.

*Primary Examiner*—Nancy Degen
*Assistant Examiner*—John S. Brusca
*Attorney, Agent, or Firm*—Dann, Dorfman, Herrell and Skillman

[57] ABSTRACT

A set of seven nuclear proteins were identified which bind to the antioxidant responsive element (ARE), a DNA sequence present in the promoters of inducible chemoprotective enzymes. One of these ARE binding proteins, here designated ARE-BP-1, has been found to exhibit binding characteristics that parallel the DNA sequences that are necessary for transcriptional induction of the chemoprotective enzymes. ARE-BP-1 is an approximately 160 kDa protein that appears to be a major control switch on the genes which act to protect cells from chemical agents. For binding by ARE-BP-1, a nucleotide sequence must include sequences outside of what was previously through to be the minimally sufficient DNA sequence for inducibility.

2 Claims, 2 Drawing Sheets

```
                              SEQUENCE LISTING

<160> NUMBER OF SEQ ID NOS: 4

<210> SEQ ID NO 1
<211> LENGTH: 18
<212> TYPE: DNA
<213> ORGANISM: human
<220> FEATURE:
<221> NAME/KEY: misc_feature
<221> NAME/KEY: misc_feature
<222> LOCATION: (4)...(5)
<222> LOCATION: (11)...(14)
<223> OTHER INFORMATION: n can be A, T, G or C
<223> OTHER INFORMATION: n can be A, T, G or C

<400> SEQUENCE: 1
tmannrtgac nnngcaww                                                18

<210> SEQ ID NO 2
<211> LENGTH: 10
<212> TYPE: DNA
<213> ORGANISM: human
<220> FEATURE:
<221> NAME/KEY: misc_feature
<222> LOCATION: (6)...(8)
<223> OTHER INFORMATION: n can be A, T, G or C

<400> SEQUENCE: 2 rtgacnnngc                                                         10

<210> SEQ ID NO 3
<211> LENGTH: 41
<212> TYPE: DNA
<213> ORGANISM: human

<400> SEQUENCE: 3
tagcttggaa atgacattgc taatggtgac aaagcaactt t                      41

<210> SEQ ID NO 4
<211> LENGTH: 41
<212> TYPE: DNA
<213> ORGANISM: human

<400> SEQUENCE: 4
tagcttggaa atgacattat taatggtgac aaaataactt t                      41
```

PROTEIN AND GENE FOR ANTIOXIDANT RESPONSE

FIELD OF THE INVENTION

The present invention relates in general to the field of cloned human genes, and relates, in particular, to the identification and use of physiologically important proteins and to the cloning and use of genes for such proteins. In this instance, the protein involved initiates the natural antioxidant response in human cells.

BACKGROUND OF THE INVENTION

The cells of higher organisms are subjected to a continuing exposure to a variety of xenobiotic hostile chemical agents. Many of these chemical agents are pro-oxidants, and free oxygen radicals are associated with detrimental events in many cell types. Accordingly, living organisms have naturally evolved biochemical detoxification mechanisms to cope with substances to which they are exposed in their environment.

Thus, higher eukaryotic life forms possess several gene families whose main purpose is detoxification of noxious chemicals. Notable among these are the glutathione S-transferases (GST) which are a ubiquitous family of isoenzymes present in all known eukaryotic species in a variety of cytosolic and membrane bound isoenzymes. Each of the GST isoenzymes displays distinct catalytic and non-catalytic binding activities and are present in many isozymes in each individual. The study of GSTs has evolved to such an extent that the cytosolic enzymes are divided into at least five distantly related gene families. Individuals have multiple isozymes from many of the families in each of their cells. The expression of GST enzymes in a given cell is stimulated by a structurally diverse range of xenobiotic agents. At lest 100 chemicals have been found that induce GST activity. A significant number of these chemical gene inducers occur naturally and are found as non-nutritive components in vegetables and citrus fruits. It has become apparent, after much study, that several systems exist in parallel to induce the transcriptional activity of GST genes, including the xenobiotic-responsive element (XRE) and the glucocorticoid-responsive element (GRE). Another well studied gene induction system which induces GST activity is known as the antioxidant-responsive element (ARE). ARE is a system active at a transcriptional level for up regulating the expression of several categories of chemoprotective enzymes in response to induction by a chemical agent.

Separately, epidemiological studies of human cancer revealed that certain substances to which humans are exposed have a statistically deterrent effect on the occurrence of cancers in human populations. Inhibition of chemical carcinogenesis by pre-exposure to protective chemical compounds was first observed over 65 years ago. One mechanism by which such compounds actuate their protective effect is by the induction of expression of GSTs. A wide variety of protective compounds have been shown to induce increased GST activity in cells and tissues. Examples of such substances include sulforaphane, natively found in cruciform vegetables such as broccoli, Oltipraz, an antischistosomal drug, and butylhydroxyanisole, or BHA, a common food preservative. The statistical demonstration that ingestion of such substances was associated with a diminution of risk of cancer led researchers into the investigation of the molecular biology of interaction of the active agents from such foods and the cancer suppression process. Thus, for example, in Wattenberg "Chemoprevention of Cancer" *Cancer Research* 45:1–8 (1985), the effect of many chemopreventive agents is discussed.

It was later proposed, and then later demonstrated to be correct, that a transcriptional activator was responsible for the initiation of chemoprotective gene families in eukaryotic cells. Early suggestions focused on the fact that multiple forms of chemical inducers could result in the induction of cancer protective enzymes. Prochaska et al., *Proc. Natl. Acad. Sci. USA*, 82:8232–8236 (1985). Later a specific antioxidant responsive element (ARE) was identified in the 5' flanking region of the rat glutathione S transferase Ya subunit gene. Rushmore et al., *J. Biol. Chem.*, 266:18:11632–11639 (1991). It was found that the ARE is responsive to a subset of antioxidants and also responsive to compounds linked to reactive oxygen species. The ARE was found to be part of a signal transduction pathway that allows eukaryotic cells to sense and respond to oxidation stress.

It was also determined that the pathway of chemoprotection is a multistep detoxification process involving at least two phases, an oxidation phase (phase I), a detoxification phase (phase II), and, possibly, a transport phase (phase III). The GST family of detoxification enzymes is induced by either of bifunctional inducers, which induce both phase I and phase II activities and by monofunctional inducers which regulate only phase II activity. Sulforaphone, Oltipraz and BHA are all monofunctional phase II inducers. Induction of the phase II enzymes GST Ya (GST1—1), NAD(P)H:quinone oxidoreductase (QR) and heme oxygenase-1 (HO-1) was shown to occur at the level of transcription. A regulatory element that mediates this increase in transcriptional rate was identified in the promoters of the rat and mouse GST Ya genes, the rat and human QR genes, and the mouse HO-1 gene. This chemoprotector inducible element has been termed the Antioxidant Responsive Element (ARE), or alternatively, the Electrophile Responsive Element. Rushmore et al. *J. Biol. Chem.*, 265:14648–14653 (1990); Friling et al. *Proc. Natl. Acad. Sci. USA*, 87:3826–3830 (1900).

Further work refined the ARE to a 30-bp element in the QR promoter and to a 41-bp element in the GST Ya promoter. All of the described ARE's were found to contain a minimal core sequence defined to be RTGACnnnGC. Daniel, *Crit. Rev. Biochem. Mol. Biol.*, 28:173–207 (1993). The term ARE core sequence, as used here, refers to this 10 bp sequence.

SUMMARY OF THE INVENTION

The present invention is summarized in that a protein designated ARE-BP-1 has been identified which binds to the genetic elements associated with antioxidant response and activates the chemoprotective enzymes in human cells.

The present invention is further characterized in that it has been discovered that the previously identified ARE associated nucleotide sequence is necessary, but not sufficient, for full ARE activity, and that an additional nucleotide sequence is sufficient.

It is an object of the present invention to identify the protein responsible for the activation of the antioxidant response in human cells.

It is a further object of the preset invention to enable the cloning and sequencing of the ARE-P-1 protein and gene so that they can be used to discover agents capable of activating the antioxidant response in humans.

It is an object of the present invention in that it suggests certain therapeutic approaches to certain disease conditions, based on the molecular data associated with the chemoprotective responsive protein.

Other objects, advantages, and features of the present invention will become apparent from the following specification when taken in conjunction with the accompanying drawings.

DETAILED DESCRIPTION OF THE INVENTION

A specific set of proteins have been identified that binds to the ARE nucleotide sequences. The proteins are here called the Antioxidant Element Response-Binding Proteins, or ARE-BP. Studies of the ARE-BP have revealed that a specific protein, here called ARE-BP-1, controls the activation of the chemoprotective response. Using the ARE-BP-1 protein in binding studies, it has been possible to identify the nucleotide sequences to which that protein will bind.

To study ARE function and associated proteins, immortal human cells in culture were transfected with a genetic construct containing a reporter gene driven by an artificial promoter which has constructed into it a mouse GST Ya ARE. The transfected cells were then exposed to tBHQ, a BHA-metabolite known to have ARE inducing properties. To determine which proteins bind to the ARE with specificity, a series of ARE binding electrophoretic mobility shift assays (EMSAs) were conducted and several retarded protein-ARE complexes were observed. EMSA is a gel based chromatography system in which radio labelled DNA fragments are slowed in their migration properties through a gel by proteins which interact with those DNA fragments. Competition EMSA studies were conducted to distinguish specific from nonspecific ARE binding proteins complexes. The specific binding proteins were found to be competed away by increasing concentrations of unlabeled ARE. The nomenclature ARE-BP-1 through ARE-BP-7 was adopted to identify each of the seven specific complexes observed, with the lowest number referring to the slowest migrating, presumably heaviest, protein complex.

Using a two-dimensional cross-linking technique described below, the approximate sizes of the ARE-BP complexes was determined. The ARE-BP-1 is approximated to be a 160 kDa protein complex, plus or minus about 5 kDa. ARE-BP-1 apparently is a multimeric complex of 2–3 homozygous subunits. Subsequent studies of ARE-BP-1 binding with a variety of nucleotide sequences revealed that ARE-BP-1 binds well to the GST Ya and QR inducer elements.

It was also of interest to determine which variants in ARE sequence were possible while retaining binding of ARE-BPs. A series of randomized altered versions of the mouse GST Ya core ARE sequence were prepared and tested in the transgenic cell system for expression of the marker gene after induction with tBHQ. Wild-type AREs from GST Ya and QR were readily induced in this system. Randomization of the two RRTGACnnGC core GST Ya ARE sequences abrogated induction. Randomization of ARE sequences outside of the ARE core sequences also abrogated induction. Combined, these results demonstrated that the previously identified minimal ARE core sequence is necessary but not sufficient for proper binding of proteins to activate the transcriptional system. Based on this insight, a study was conducted which interactively examined the binding characteristics of the ARE-BP proteins with variants of the ARE sequences to which they would bind.

Figure 1:
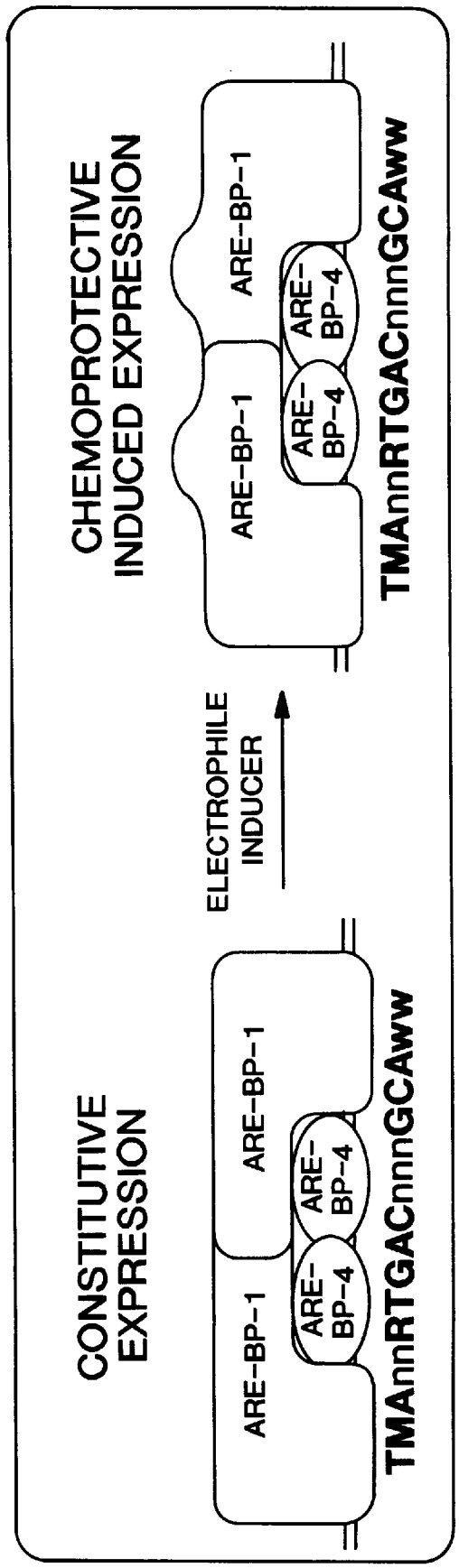
FIG. 1 is a schematic illustration of how ARE-BP-1 is proposed to bind to an ARE (SEQ. ID NO: 1).

This study has suggested the model for antioxidant response induction shown in FIG. 1. The ARE-BP-1 and ARE BP-4 proteins are both constitutively expressed and bind in the area of the ARE. It is believed the ARE-BP-4 actually binds to the minimal RTGACnnnGC (SEQ. ID NO: 2) site previously though to be sufficient for ARE induction. Also binding cis to this region is ARE-BP-1. The sequences in ARE important to binding of ARE-BP-1 are shown in capital letters in FIG. 1, with "M" meaning c or A and "ww" meaning a preference, but not a requirement, for A or T. The initiation of transcription activity is thought to be associated with a induced change in the ARE-BP-1 protein. In other words, the ARE-BP-1 proteins sits on the ARE DNA, but is inactive until an inducing chemical acts to initiate a response which alters the ARE-BP-1 protein in place. This mechanism might be a direct interaction between the electrophile and the ARE-BP-1 protein, in which the ARE-BP-1 protein alters itself in response to interaction with the electrophile, or might be the result of an intermediate protein which senses the electrophile and then activates ARE-BP-1. In any event, transcription of the ARE-BP-1 gene does not appear to be activated by the electrophile, but when the protein ARE-BP-1 is activated by presence of the chemical agent, transcription activity of the chemoprotective enzymes is then induced.

It should be stated clearly that the model shown in FIG. 1 is just a model. It is demonstrated here by te data below that ARE-BP-1 is important for the induced chemoprotective response, that it is present prior to induction, and that it binds specifically to inducible sequences. The exact mechanism by which ARE-BP-1 is itself activated to initiate induction is not yet known.

It was thus found that sequences outside of the minimal ARE are required for ARE-BP-1 binding and such binding specifically requires a GC-box associated with the ARE. For example consider the two sequences:

(A) TAGCTTGGAAATGACATTGCTAATGGT-GACAAAGCAAACTTT (SEQ. ID NO: 3)

(B) TAGCTTGGAAATGACATTATTAATGGT-GACAAATAACTTT (SEQ. ID NO: 4)

It was found that ARE-BP-1 avidly binds to sequence A, the native sequence from murine GST Ya, but fails to bind to sequence B, the same sequence with mutation indicated by the underlines, the mutations occurring in he GC-boxes. To test the limits of such variation, a series of oligonucleotides was tested against ARE-BP-1 to determine the variants in sequence to which the protein would bind. The ARE-BP-1 was found to bind generally to a consensus sequence RYAAC (R being G or A while Y is C or T). This consensus sequence corresponds to the GCA ww sequence in FIG. 1, where the preferred G and C are shown. This information solves a quandary in our knowledge of the ARE element. Researchers have commonly found the minimal RTGACnnnCGA sequence in a variety of newly isolated genes, but not all of which appear to be inducible by the ARE system. The identification of the ARE-BP-1 protein permits such sequences to be tested or simply analyzed, for ARE functionality, by determining if the sequences necessary for ARE-BP-1 binding are present.

The identification of the ARE-BP-1 protein provides important insight to the development of new agents to induce chemoprotective effects. Chemicals can be tested for their direct ability to alter the ARE-BP-1 protein to induce transcriptional activity. It may become desirable to increase the presence of ARE-BP-1 in certain patients, as a protein or through gene therapy, to increase the resistance of cells to chemotherapeutic agents. Alternatively, by blocking the expression of ARE-BP-1 in cancer cells, those cells may be rendered more susceptible to chemotherapeutic agents.

The identification of the important ARE-BP-1 protein also will enable the sequencing of the protein and the isolation and cloning of the gene for ARE-BP-1. It is now possible to purify the ARE-BP-1 protein from its host using the criteria specified here. N-terminal sequencing can then be performed on the protein, thereby allowing DNA probes to be designed to recover either the cDNA or the genomic clone for ARE-BP-1. The cloning of the ARE-BP-1 gene makes possible the insertion of the gene into heterologous hosts either for the purpose of making purified ARE-BP-1 protein or for the purpose of gene therapy for a clinical disease.

Since ARE-BP-1 is a critical part of our body's defense against chemically-induced cancer, it is quite possible that one factor in the susceptibility of families to cancers induced by environmental agents is the allele of ARE-BP-1 carried by members of the family. It is likely that persons with a null/null ARE-BP-1 genotype are at a heightened risk for chemically induced cancer, a risk which could be ameliorated by therapeutic introduction of the protein or the gene. Genetic testing for such susceptibility also becomes possible.

The availability of the ARE-BP-1 protein makes possible an intelligent form of drug selection. Since ARE-BP-1 is the master switch of the ARE-mediated chemoprotective response system, activating the protein artificially would presumably lessen an individual's risk of incurring cancer. ARE-BP-1 can now be purified in reasonable amounts, either by purification from a host or by making the protein recombinantly in a heterologous host. Then potential drug agents intended to induce activation of the chemopreventive response can be exposed to the ARE-BP-1 to test to see if the agent activates the ARE-BP-1. In this way, potentially effective cancer prophylactic drugs become testable.

The ARE-BP-1 can also be used to identify and test other potential ARE elements. Since ARE-BP-1 binds specifically to parts of the ARE sequence necessary for inducible activity, probing other nucelotide sequences with ARE-BP-1 will reveal which sequences have the necessary sequence to be ARE's.

For patients deficient in ARE-BP-1, additional protein can be delivered to the patient, either as protein or as gene therapy. Conversely, it may be desirable to down-regulate ARE-BP-1 production in the cancer cells in an individual. This can be done by several techniques well known to the art.

EXAMPLES

Reporter cells

To facilitate the study of the ARE system and its variants, a reported cell system was used based on transgenic human cells in culture. Hep G2 hepatoma cells were grown in Dulbecco's Modified Eagle's Medium with high glucose/F-12/fetal bovine serum (4.5:4.5:1) with the antibiotic gentamycin included at 50 $\mu$g/ml. The cells were grown at 37° C. with 7% atmosphere $CO_2$.

An expression vector for the reporter gene luciferase was constructed with the 41 bp GST mouse Ya ARE inserted into the pTI-luc promoter (pARE-TI-luc). This construct was transformed into the Hep G2 cells by calcium phosphate co-precipitation with a 2-min glycerol shock performed 5 hr. after addition of the precipitate to dishes.

To induce reporter gene activity, 16 hr after the glycerol shock, the dishes with the cells were treated with 60 $\mu$M terti- buylhydroquinone (Fluka) or tBHQ, for 20–24 hors. To test for luciferase activity, the cells were harvested with trypsin, lysed, and membranes precipitated by centrifugation at 13,000×g for 10 min. The supernatants were used for luciferase assays and the results were internally standardized relative to beta-galactosidase enzyme assay results. Transfections and assay were done in triplicate.

Luciferase activity was discernably higher than background at 4 hours, and after 24 hours of continuous exposure to tBHQ, the induced luciferase activity was 11-fold higher than in solvent treated cells. Thus the HepG2 cells exhibited all the components necessary for ARE-mediated chemoprotective response.

Interaction of nuclear proteins with ARE DNA

Nuclear extracts were prepared by a modification of the procedure described by Dignam et al., *Nucleic Acids Res.*, 11:1475–1489 (1983).

To determine whether proteins from nuclear extracts within the Hep G2 cells bind to ARE with specificity, a series of ARE binding electrophoretic mobility assays (EMSAs) was performed. The procedure used was based on Costa et al. *Mol. Cell. Biol.*, 8:81–90 (1988). Nuclear extracts from untreated HewpG2 cells were mixed with 3 ng of $^{32}$P-end-labelled 41-bp GST Ya ARE probe. This gel compared the mobility of the ARE DNA probe alone to the mobility of the ARE DNA probe after mixing the probe with nuclear proteins. The object was to find which proteins would slow the migration of the ARE DNA probe due to protein-DNA interaction. Seven retarded protein-DNA complexes were observed which were specific in that they retarded migration of the ARE DNA probe, but not by other DNA, such as the Rel Related Binding Site probe, an NFkB site. Non-specific bands ere ignored. The seven retarded bands were designated ARE-BP-1 through ARE-BP-7, in order of slowest migration to fastest migration. The band for ARE-BP-4 was wider and more diffuse than the other bands, suggesting that multiple binding activities might be present.

ARE proteins during induction

This study was conducted to determine the change in the abundance of the ARE-BP proteins during actual induction of the ARE system. HepG2 cells were exposed to 60 $\mu$M tBHQ for 0 to 24 hours, followed by nuclear protein extraction and EMSA analysis. It was found that tBHQ treatment had no discernable effect on the intensity of any of the ARE-BP bands and no additional bands were detected. This results suggested that the ten-fold induction response mediated by the ARE is not dependent on a newly expressed trans activator nor by an increased nuclear concentration of a trans activator. All of the required transcription factors appeared to be expressed constitutively in the cells and bound to the ARE.

Determining protein size

Because the seen ARE-BP protein complexes run in close proximity in the native gel-shift lanes, cross-linking and retrieval of individual gel-shift bands was difficult. To minimize this problem and to accurately determine molecular weights for the seen protein complexes, a two-dimensional cross-linking procedure was performed. In the first electrophoretic dimension, protein-DNA complexes were separated using standard gel shift conditions. In this extended gel shift, the ARE-BP-4 bands was resolved into multiple bands, referred to as ARE-BP-4A and ARE-BP-4B. After UV-crosslinking of the protein-DNA complexes with the intact gel, an entire lane was excised and placed on top of an SDS-PAGE gel. The convalently linked ARE-BP complexes were then separated in the denaturing dimension on the basis of molecular weights. The approximate sizes of the various ARE-BP proteins was then determined by subtracting the molecular weight of the ARE probe from the observed weight of the DNA/protein complex in the gel. The calculated sizes of the ARE-BP proteins determined by this method are set forth in the following Table 1.

TABLE 1

Sizes of individual, Uv-crosslinked ARE-BPs

| ARE-BP | UV-Crosslink Analysis Corrected Protein Size (kDa) | Ferguson Analysis Protein Complex Size (kDa) |
|---|---|---|
| 1 | 160 (5)[a] | 395 (40)[a] |
| 2 | 81 (2) | 270 (30) |
| 3 | 121 (3) | 130 (10) |
| 4A | 40 (3) | N.D.[b] |
| 4B | 67 (2) and 108 (4) | 170 (10) |
| 5 | 58 (3) | 115 (10) |
| 6 | 70 (2) and 81 (2) | 80 (10) |
| 7 | 27 (3) | 50 (5) |

[a]Indicated standard error values are based upon three determinations.
[b]ARE-BP-4A could not be distinguished in the higher acrylamide percentage Ferguson gels.

The observed size of the ARE-BP-4A protein (40 kDa) is consistent wit the known size of the AP-1 family of transcriptional activators. The relative positions on the gel for all the protein complexes were supported by additional cross-linking studies.

Ferguson analysis was then conducted on the native ARE-BP complexes to determine the total native size of the ARE-BP-DNA complexes. Taking the UV-cross-linking subunit sizes into consideration, several of the complexes sizes are indicative of the presence of multiple protein subunits in he ARE-protein complex. The agreement between the UV-cross-linking and Ferguson analysis sizes for some ARE-BPs (e.g. ARE-BP-3 and ARE-BP-6) suggests a monomeric structure. For ARE-BP-1, a multimeric structure was indicated.

Study of affinity for ARE binding

This study began with the objective of determining the regions of the GST Ya ARE to which the ARE-BPs bind to determine if binding associates with induction of chemoprotective response. For this study, a group of wild-type AREs, ARE mutants and ARE regions were used as competitors in gel shift analysis. In such competition, a binding competitor is indicated by the absence or diminution of an otherwise present band containing an ARE-BP. It was found that the different ARE-BP species had different binding characteristics for variants in the ARE sequence. The most striking result in this analysis was the observation that the ARE-BP-1 species was strongly competed for by both the ARE Ya and ARE QR elements and 20 bp from the 3' end of the GST Ya ARE sequence. However, ARE-BP-1 was not competed for by elements containing a mutation (AT instead of GC) in the "GC-box" portion of the ARE sequence. This pattern differs significantly from the other proteins. For example, ARE BP-6, the most prominent band in the gel, follows a dramatically different pattern, being competed for both by an inactive ARE element with randomized sequence outside of the core sequence, and by the "GC-box" mutant. This pattern for ARE-BP-6 is inconsistent with the pattern expected for a factor mediating the chemoprotective response.

Figure 2:
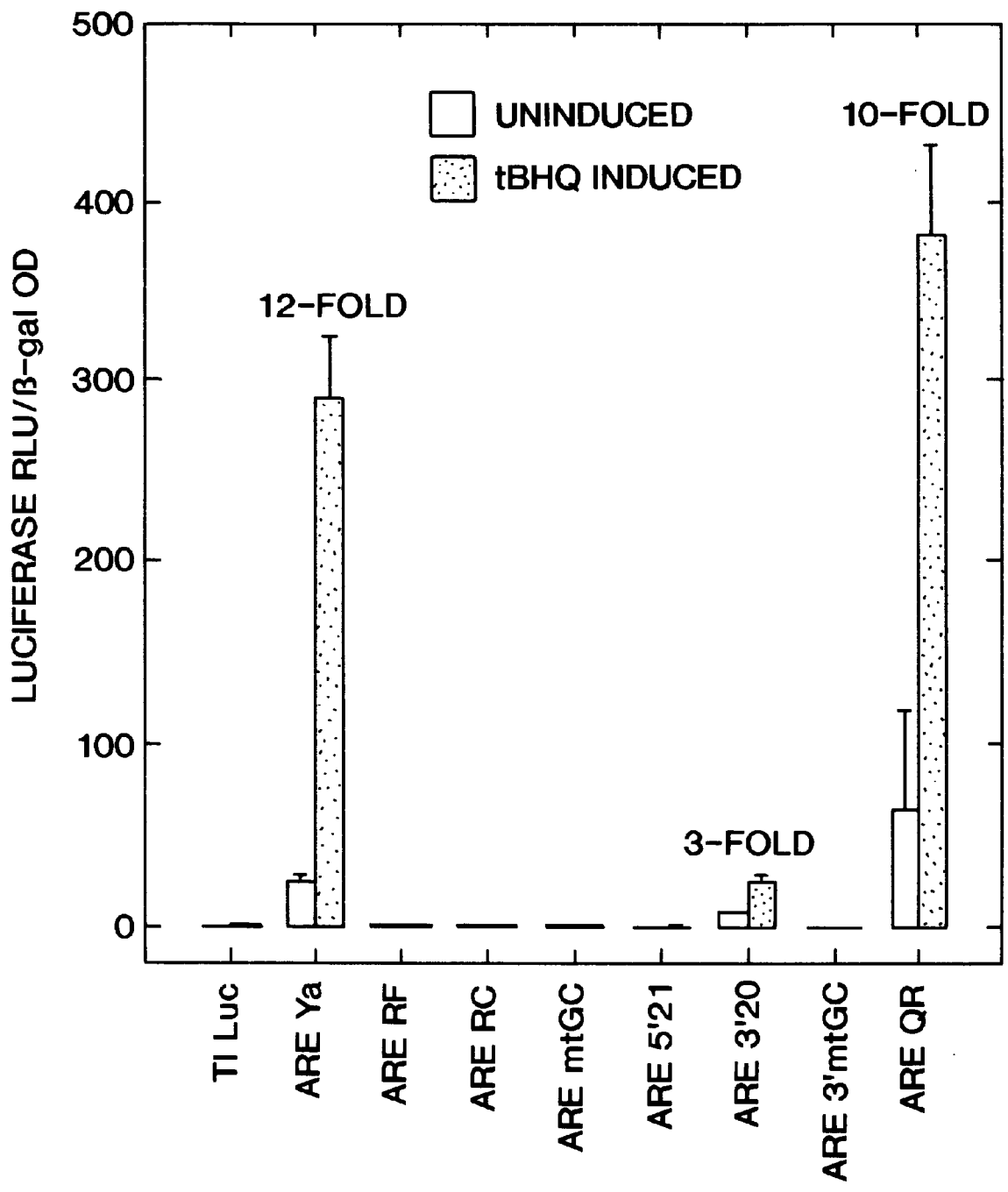
FIG. 2 is a graphical presentation of data from a part of the Examples below.

To correlate the binding characteristics of the ARE-BP proteins with the actual chemoprotective response, DNA sequences were cloned in a reporter gene system. The DNA coding sequence for the ARE variants were inserted into an SmaI site in the minimal promoter luciferase expression vector pTI-luc. The constructs were transfected into HepG2 cells and the cells were then treated with either tBHQ or a solvent. The data is shown in FIG. 2. The wild-type AREs from the GST Ya and QR promoters were highly induced. Randomization of the two RRTGACACnnnGC (designated ARE RC) and the non-core flanking sequence (ARE RF) were complete failures. The failure of the randomized flanking ARE RF mutant to mediate induction clearly demonstrated that there are additional cis-acting sequences outside of the RTGCAnnnCG (SEQ. ID NO: 2) core region that are necessary for inducibility. The 41-bp "GC-box" mutant was not inducible and had very low basal activity. A 5' 21bp fragment of ARE (ARE 5' 21bp) was found not to be inducible despite the presence of the complete 5' RTGACnnnGC core element.

The relative binding of the ARE-BP proteins to the variants and the inducibility of the variants is presented in tabular form in Table 2 below. Only the binding activities of ARE-BP-1 and ARE-BP-2 are consistent with that expected for a protein which productively interacts with the ARE to actually mediate the chemoprotective induction response. In Table 3, ARE 3'mtGC is a GC box mutant only at the 3' end.

TABLE 2

Summary of ARE-BP binding and induction supported by ARE variants

| ARE Variant | tBHQ Induci- bility[a] | ARE-BP Binding to Specified ARE Variants[b] | | | | | | |
|---|---|---|---|---|---|---|---|---|
| | | BP-1 | BP-2 | BP-3 | BP-4 | BP-5 | BP-6 | BP-7 |
| ARE Ya | +++ | + | + | + | + | + | + | + |
| ARE RF | − | − | − | + | + | − | + | + |
| ARE RC | − | − | − | + | − | − | − | − |
| ARE "GC box" mt | − | − | − | + | + | + | + | + |
| ARE 5' 21 bp | − | − | − | + | − | − | − | − |
| ARE 3' 20 bp | + | + | + | − | + | − | − | − |
| ARE 3' mt GC | − | − | − | − | + | − | − | − |
| ARE QR | +++ | + | + | + | + | + | − | − |

+ indicates moderate induction (2–6 fold), and − indicates no induction (<2 fold)

Note the BP-2, which is faint on the gels and not much smaller in size that ARE-BP-1, exhibits binding properties identical to ARE-BP1. The best explanation is that ARE-BP-2 is actually an altered species of ARe-BP-1, perhaps being a protease degradation product, a splice variant or a homologous protein. The term ARE-BP-1 is used here to refer to both variants and others which exhibit the same binding characteristics.

Subsequent analysis revealed the presence of the ARE-BP-1 protein in other immortal cell lines (a murine cell line Hepa1c1c7 and a human cell line HeLa). Thus the ARE-BP-1 is believed to be relatively conserved, and ubiquitous.

The best explanation for the observed data is that the bands here designated ARE-BP-4 correspond to the AP-1 factors known to bind to the ARE. However, the data does not support the notion that AP-1 has a primary role in actual ARE-mediated induction since the ARE-BP-4 binds to several non-inducible ARE variants. In this light, it appears that although AP-1, or ARE-BP-4, may be a transcriptional factor, it is not the determinative factor in inducing the chemoprotective response. That role appears to belong to ARE-BP-1.

FIG. 1 illustrate a hypothesis for the interaction of these elements that fits the observed data. The ARE-BP-4 protein binds to the minimal ARE element. The ARE-BP-1 protein binds cis to the ARE element, including at the GC-box. Both proteins are expressed constitutively and bound to the ARE, even in the absence of induction. Then, induction cause some change in the ARE-BP-1 molecule turning it from inactive to active. Transcription of chemoprotective enzyme family then commences.

We claim:
1. A preparation comprising human ARE-BP-1 protein purified from a host cell.

2. A composition of matter comprising human ARE-BP-1 protein isolated from other proteins and from any host cell.

* * * * *